(12) United States Patent
Nakahara et al.

(10) Patent No.: US 8,168,851 B2
(45) Date of Patent: May 1, 2012

(54) ADHESIVE SKIN PATCH SHEET

(75) Inventors: Kaname Nakahara, Tokyo (JP); Atsuko Kameshima, Tokyo (JP)

(73) Assignee: Lintec Corporation, Tokyo (JP)

( * ) Notice: Subject to any disclaimer, the term of this patent is extended or adjusted under 35 U.S.C. 154(b) by 618 days.

(21) Appl. No.: 12/289,923

(22) Filed: Nov. 6, 2008

(65) Prior Publication Data

US 2009/0124953 A1    May 14, 2009

(30) Foreign Application Priority Data

Nov. 8, 2007    (JP) ................. 2007-290643

(51) Int. Cl.
*A61F 13/00*    (2006.01)
(52) U.S. Cl. .......................................... 602/57; 602/52
(58) Field of Classification Search ............. 602/41–59; 206/440, 441; D24/189
See application file for complete search history.

(56) References Cited

U.S. PATENT DOCUMENTS

| | | | | |
|---|---|---|---|---|
| 2,823,672 | A * | 2/1958 | Schladermundt et al. | 602/57 |
| 3,425,412 | A * | 2/1969 | Pope | 602/59 |
| 4,619,253 | A * | 10/1986 | Anhauser et al. | 602/42 |
| 5,266,371 | A * | 11/1993 | Sugii et al. | 428/41.5 |
| 5,419,913 | A * | 5/1995 | Podell et al. | 424/448 |
| 6,319,515 | B1 * | 11/2001 | Hidaka et al. | 424/449 |
| 6,841,716 | B1 * | 1/2005 | Tsutsumi | 602/57 |
| D545,441 | S * | 6/2007 | Miyachika et al. | D24/189 |
| 7,910,792 | B2 * | 3/2011 | Iwahashi et al. | 602/54 |
| 2006/0099241 | A1 * | 5/2006 | Saito | 424/447 |

* cited by examiner

*Primary Examiner* — Kim M Lewis
(74) *Attorney, Agent, or Firm* — Posz Law Group, PLC

(57) ABSTRACT

An adhesive skin patch sheet comprises a support, a pressure-sensitive adhesive layer and a release sheet laminated in that order, the release sheet is divided by a cut line into a small first release sheet and a large second release sheet, the cut line is formed so as to be convex only from the second release sheet toward the first release sheet.

7 Claims, 5 Drawing Sheets

Fig.5
(a)
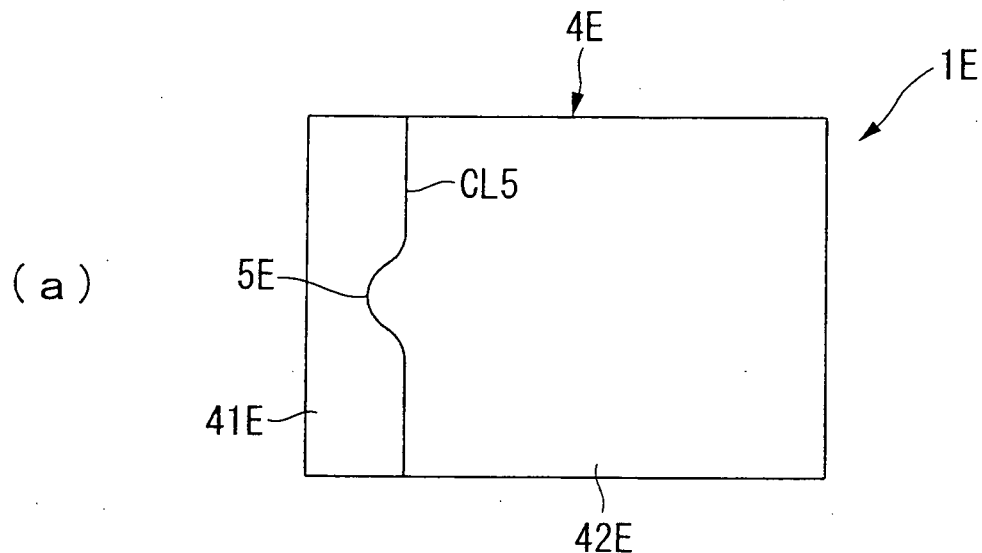
(b)
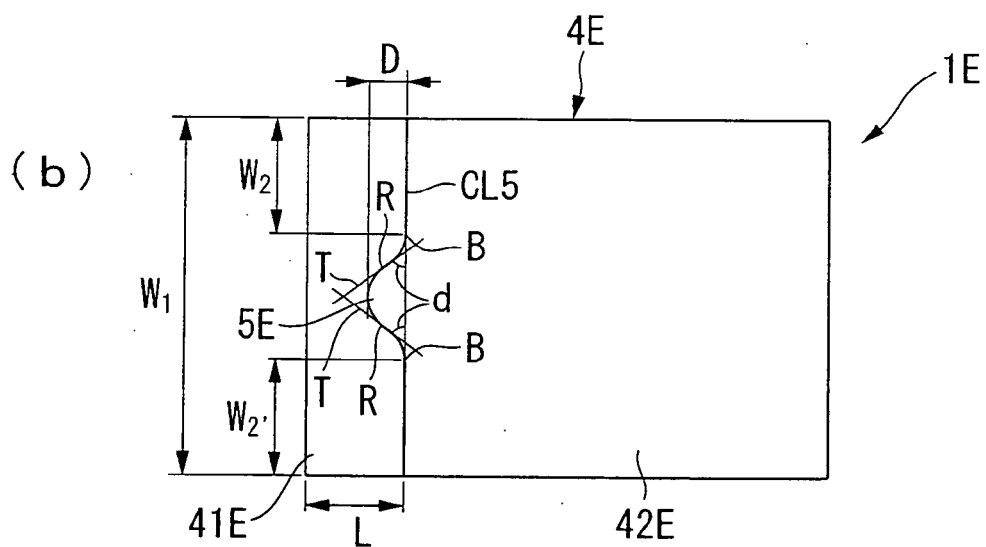

Fig.6
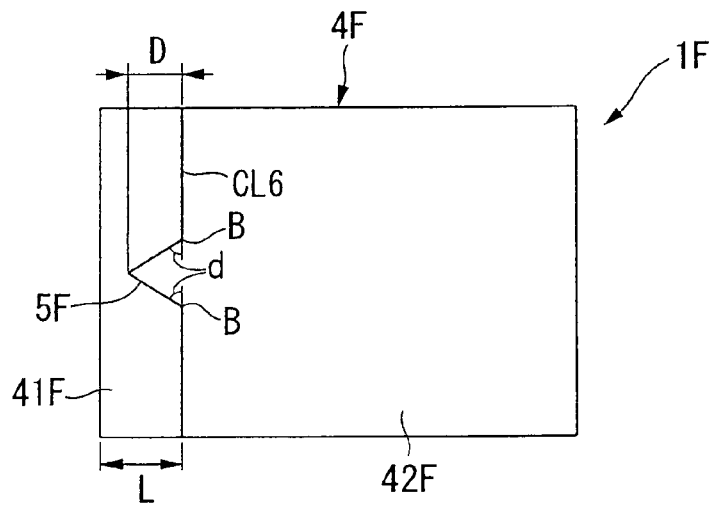
Fig.7
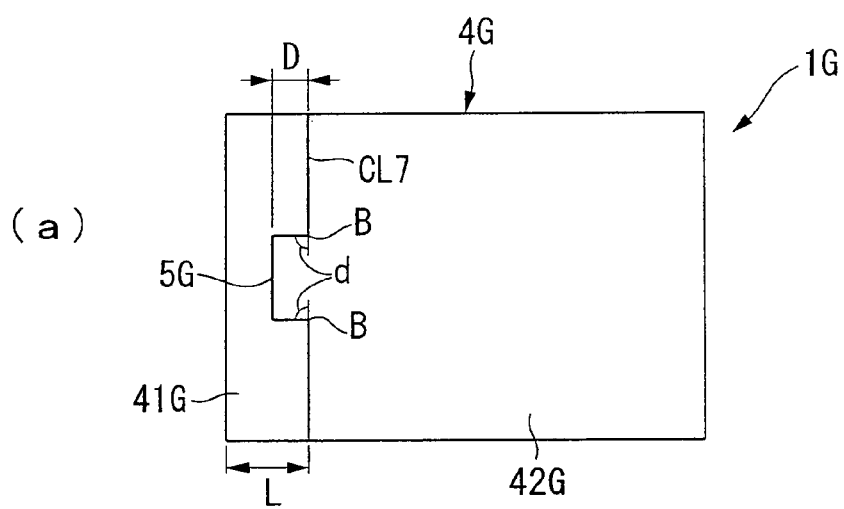
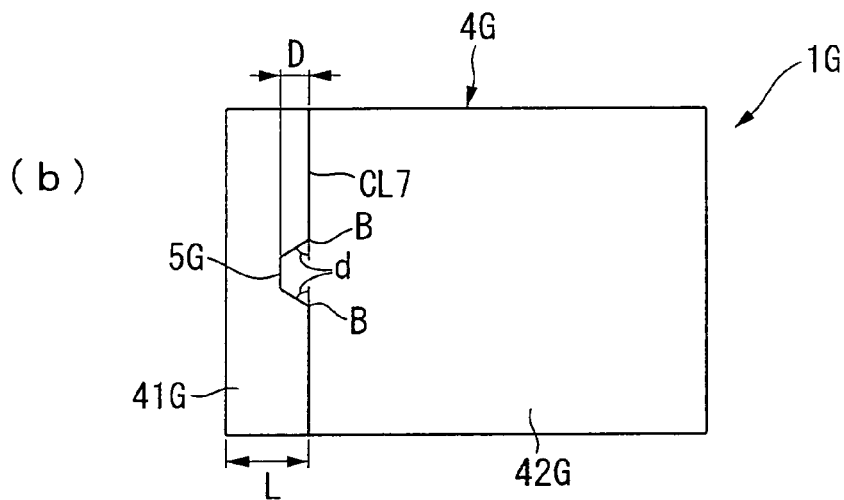

ADHESIVE SKIN PATCH SHEET

BACKGROUND OF THE INVENTION

1. Field of the Invention

The present invention relates to an adhesive skin patch sheet that is applied, for instance, onto the skin surface.

2. Description of the Related Art

Known adhesive skin patch sheets applied onto the skin surface include, for instance, adhesive skin patches such as anti-inflammatory analgesic adhesive patches or the like for transdermal administration of a medicinal agent with a view to, for instance, treating a condition. Such adhesive skin patch sheets comprise ordinarily a flexible support, for following the skin contour; a pressure-sensitive adhesive layer containing the medicinal agent, formed on the support; and a release sheet for protecting the pressure-sensitive adhesive layer until use of the adhesive skin patch sheet.

To use the adhesive skin patch sheet, the release sheet is peeled off and the pressure-sensitive adhesive layer exposed thereby is applied onto the skin surface. However, the support is flexible and thus difficult to hold in the hand. As a result, the adhesive skin patch sheets bends when attempting to apply the whole pressure-sensitive adhesive layer in one go after peeling off the entire release sheet, which gives rise to problems such as adhesion between pressure-sensitive adhesive layers, and wrinkling of the adhesive skin patch sheet applied onto the skin surface.

Adhesive skin patch sheets have been proposed in which straight-line or wavy cuts are made on the release sheet, dividing thereby the release sheet in two, with a view to enhancing the handleability of the adhesive skin patch sheet (Japanese Utility Model Registration Nos. 2596722, 2597846, Japanese Utility Model Application Laid-open No. 58-124123). To use such adhesive skin patch sheets, one of the release sheets (first release sheet) is peeled off and the exposed half pressure-sensitive adhesive layer is applied onto the skin surface, whereafter the adhesive skin patch sheet is bent, and the other release sheet (second release sheet) is gradually peeled, from the inner end thereof toward the outer end, at the same time that the exposed pressure-sensitive adhesive surface is gradually applied onto the skin surface. Such adhesive skin patch sheets are easier to handle than those in which the whole pressure-sensitive adhesive layer is applied in one go after having peeled off the entire release sheet.

Adhesive skin patch sheets where the release sheet is cut with a straight line cut, however, are problematic in that the second release sheet lacks a portion that can be picked with the fingers when peeling the second release sheet, from the inner end thereof to the outer end, after having applied half of the pressure-sensitive adhesive layer onto the skin surface, so that the second release sheet is difficult to peel off.

Adhesive skin patch sheets where the release sheet is cut with a wavy cut, on the other hand, are advantageous in that the second release sheet has a portion that can be picked with the fingers when peeling off the second release sheet, from the inner end thereof to the outer end, after having applied half of the pressure-sensitive adhesive layer onto the skin surface, so that the second release sheet is easy to peel off. Such adhesive skin patch sheets, however, are often prone to wrinkle during applying of the second half of the adhesive skin patch sheet. This wrinkling is believed to be caused by the wavy end edge of the second release sheet.

SUMMARY OF THE INVENTION

In light of the above, it is an object of the present invention to provide an adhesive skin patch sheet excellent in handleability and little prone to form wrinkles during applying.

To attain the above object, the present invention provides an adhesive skin patch sheet comprising a flexible support, a pressure-sensitive adhesive layer and a release sheet, wherein only one cut is provided on either an X-axis direction or a Y-axis direction of the release sheet, the release sheet being divided by the cut into two, a large release sheet and a small release sheet, and a line making up the cut being formed so as to be convex only from the large release sheet toward the small release sheet (invention 1).

The X-axis direction of the release sheet denotes herein one predetermined direction in the plane direction of the release sheet. The Y-axis direction of the release sheet denotes a direction perpendicular to the X-axis direction. When only one cut is provided in the X-axis direction (or Y-axis direction) of the release sheet of the present invention, it is preferable that no cut be provided in the Y-axis direction (or X-axis direction) of the large release sheet and/or the small release sheet, although one or plural such cuts may be provided.

To use the adhesive skin patch sheet according to the above invention (invention 1), the small release sheet (first release sheet) is peeled off and the pressure-sensitive adhesive layer exposed thereby is applied, followed by peeling of the large release sheet (second release sheet). Peeling first the small release sheet results in a smaller exposed portion of the pressure-sensitive adhesive layer. The adhesive skin patch sheet can be handled more easily as a result, while making wrinkling less likely during applying of the exposed portion of the pressure-sensitive adhesive layer. After applying the pressure-sensitive adhesive layer exposed through peeling of the first release sheet, the adhesive skin patch sheet is bent, around along the cut line, on the side of the support, whereupon there juts out a convex portion at the inner end of the second release sheet. This portion can be picked with the fingers, whereby the second release sheet can be easily peeled off. Moreover, shaping the second release sheet so as to be convex only toward the first release sheet reduces the likelihood of nonuniform release force between the second release sheet and the pressure-sensitive adhesive layer. This suppresses as a result wrinkling of the adhesive skin patch sheet when applying the pressure-sensitive adhesive layer while peeling the second release sheet off.

In the above invention (invention 1), preferably, the pressure-sensitive adhesive layer and the release sheet are substantially shaped, in a plan view, as rectangles of substantially identical size, and both ends of the line making up the cut are respectively located at positions distant from ends of two opposing sides of the release sheet by $1/3$ to $1/20$ of the length thereof (invention 2).

By forming the cut line at such positions, the surface area of the pressure-sensitive adhesive layer exposed when the first release sheet is peeled off is small enough so as to prevent wrinkling of the adhesive skin patch sheet during applying the first half of the adhesive skin patch sheet.

In the above inventions (inventions 1 and 2), preferably, the length of a convexity of the line making up the cut in the convex direction (distance in the convex direction between the most convex point of the line making up the cut and the most distant point, in the convex direction, from the most convex point) is 5 to 25 mm (invention 3).

According to the above invention (invention 3), the jutting portion (convex portion) of the second release sheet has a size that allows the jutting portion to be easily picked with the fingers when peeling the second release sheet off.

In the above inventions (inventions 1 to 3), preferably, the line making up the cut may be wholly convex from the large release sheet toward the small release sheet (invention 4), alternatively, the shape of the line making up the cut may have a convexity that is partially convex from the large release sheet toward the small release sheet (invention 5).

In the above invention (invention 5), preferably, the convexity rises from base points respectively located at positions distant by 1/3 to 1/50 of the length of the release sheet in the direction of the line making up the cut, from the ends of the line (invention 6).

By forming the rising portions of the convexity at the above-described positions, the convexity has a predetermined width at a non-edge position, which enables a smooth transition from peeling of the convexity to peeling of portions other than the convexity, in the second release sheet. This reduces, as a result, the likelihood of nonuniform release force between the second release sheet and the pressure-sensitive adhesive layer, and suppresses thereby the formation of wrinkles in the adhesive skin patch sheet.

In the above inventions (inventions 5 and 6), preferably, the line making up the cut comprises the convexity and a straight-line portion other than the convexity, and an angle formed between the straight-line portion and the line making up the convexity or a tangent of the line making up the convexity, on the inward side of the convexity, being the largest angle, ranges from 5° to 90° (invention 7).

By having such a shape, the convexity enables a smooth transition from peeling of the convexity to peeling of the straight-line portion, in the second release sheet. This reduces, as a result, the likelihood of nonuniform release force between the second release sheet and the pressure-sensitive adhesive layer, and suppresses thereby the formation of wrinkles in the adhesive skin patch sheet.

The adhesive skin patch sheet of the present invention is excellent in handleability and little prone to form wrinkles during applying.

BRIEF DESCRIPTION OF THE DRAWINGS

FIGS. 5(a) and 5(b) are bottom plan views of an adhesive skin patch sheet according to a fifth embodiment of the present invention;

FIG. 6 is a bottom plan view of an adhesive skin patch sheet according to a sixth embodiment of the present invention;

FIGS. 7(a) and 7(b) are bottom plan views of an adhesive skin patch sheet according to a seventh embodiment of the present invention;

DESCRIPTION OF THE PREFERRED EMBODIMENTS

Embodiments of the present invention are explained below.

First Embodiment

Figure 1:
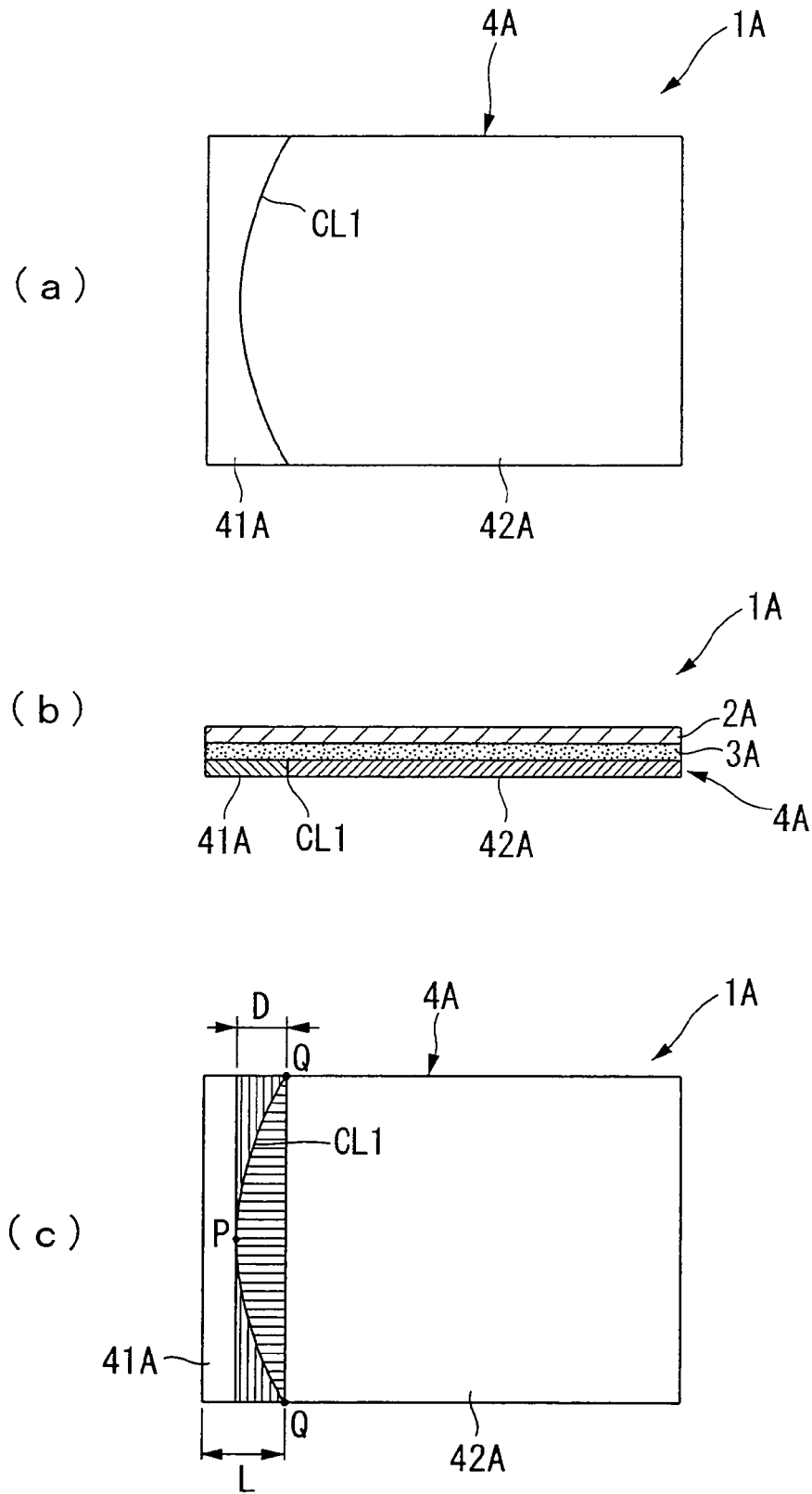
FIGS. 1(a) and 1(c) are bottom plan views of an adhesive skin patch sheet according to a first embodiment of the present invention, FIG. 1(b) being a cross-sectional view thereof.

FIGS. 1(a) and 1(c) are bottom plan views of a adhesive skin patch sheet according to a first embodiment of the present invention, and FIG. 1(b) is a cross-sectional view thereof.

As shown in FIG. 1(b), an adhesive skin patch sheet 1A according to the present embodiment comprises a support 2A, a pressure-sensitive adhesive layer 3A and a release sheet 4A, laminated in this order. As shown in FIG. 1(a), the adhesive skin patch sheet 1A has an overall rectangular shape in a plan view. The support 2A, the pressure-sensitive adhesive layer 3A and the release sheet 4A have all substantially the same shape and size, although the present invention is not limited thereto.

The size of the adhesive skin patch sheet 1A may be appropriately selected in accordance with, for instance, the intended use of the adhesive skin patch sheet 1A. When the adhesive skin patch sheet 1A is used, for instance, as an anti-inflammatory analgesic adhesive patch applied to the skin surface, the sides of the adhesive skin patch sheet 1A in the longer side direction thereof (horizontal direction in FIG. 1(a), likewise hereinafter) range from 70 to 200 mm, preferably, in particular, from 100 to 200 mm. The sides of the adhesive skin patch sheet 1A in the width direction thereof (vertical direction in FIG. 1(a), likewise hereinafter) range from 50 to 150 mm, preferably, in particular, from 70 to 140 mm.

The support 2A comprises a flexible material. When the adhesive skin patch sheet 1A is applied, for instance, onto the skin surface, the flexible support 2A allows the adhesive skin patch sheet 1A to hug easily the skin contour. The material of the support 2A may also be a contractile material.

Examples of materials that can be used as the material of the support 2A include, for instance, conventionally used materials such as thermoplastic elastomer films of polystyrene; films of polyolefins such as polyethylene, polypropylene, ethylene/methacrylic acid copolymers, ethylene/methyl methacrylate copolymers or the like; resin films such as polyurethane films, polyester films or the like; woven fabrics, knitted fabrics and nonwoven fabrics of various synthetic fibers and/or natural fibers; as well as paper and laminates of the foregoing.

The thickness of the support 2A may be appropriately selected in accordance with, for instance, the intended use of the adhesive skin patch sheet 1A, but, preferably, ranges ordinarily from 10 to 1000 μm, and in particular from 20 to 800 μm.

The material used as the material of the pressure-sensitive adhesive layer 3A may be a conventionally known material appropriately selected in accordance with, for instance, the intended use of the adhesive skin patch sheet 1A. When the adhesive skin patch sheet 1A is applied, for instance, onto the skin surface, the material used in the pressure-sensitive adhesive layer 3A may ordinarily be a pressure-sensitive adhesive such as a rubber based pressure-sensitive adhesive, an acrylic based pressure-sensitive adhesive, a silicone based pressure-sensitive adhesive or the like. Depending on the intended use of the adhesive skin patch sheet 1A, the pressure-sensitive adhesive may contain a medicinal agent, as well as a tackifier, a softener, an antioxidant and the like, as desired.

The thickness of the pressure-sensitive adhesive layer 3A may be appropriately selected in accordance with, for instance, the intended use of the adhesive skin patch sheet 1A, but, preferably, ranges ordinarily from 20 to 1000 µm, and in particular from 30 to 300 µm.

The adhesive strength of the pressure-sensitive adhesive layer 3A may be appropriately set in accordance with, for instance, the intended use of the adhesive skin patch sheet 1A. For instance, when the adhesive skin patch sheet 1A is applied onto the skin surface, the adhesive strength of a pressure-sensitive adhesive sheet comprising the pressure-sensitive adhesive layer formed to a thickness of 40 µm on a 50 µm-thick polyethylene terephthalate film, the pressure-sensitive adhesive sheet being applied onto bakelite, and being tested for adhesive strength 5 minutes thereafter in accordance with JIS Z0237, is preferably 0.2 to 20 N/25 mm, in particular 0.5 to 15 N/25 mm.

The material used as the material of the release sheet 4A is not particularly limited and may be a conventionally known material, provided that it can protect the pressure-sensitive adhesive layer 3A and can be peeled therefrom, and provided that it is stiffness enough to allow a convex portion of the release sheet 4A to jut out when the adhesive skin patch sheet 1A is bent, on the side of the support 2A, along a below-described cut portion of the release sheet 4A.

As regards the stiffness of the release sheet 4A, the bending resistance thereof according to JIS L1096-1999 (45° cantilever method) ranges preferably from 40 to 150 mm, in particular from 60 to 140 mm.

The release sheet 4A used may be, for instance, a resin film such as polyester film of polyethylene terephthalate, polyethylene naphthalate or the like, a polyolefin film of polypropylene, polymethylpentene or the like, or a polycarbonate film; or paper such as glassine, clay coated paper, or laminated paper (chiefly polyethylene laminated paper) that has been subjected to a release treatment with release agent such as a silicone based one, a fluorine based one, or a long chain alkyl group-containing carbamate.

The thickness of the release sheet 4A varies depending on the material thereof, but ranges preferably from 25 to 200 µm, in particular from 38 to 100 µm, in order to exhibit the above stiffness.

As shown in FIG. 1(a), the release sheet 4A is divided by way of a cut into a small release sheet 41A (hereinafter "first release sheet 41A", on the left of FIG. 1(a)), and a large release sheet 42A (hereinafter "second release sheet 42A", on the right of FIG. 1(a)). In the figure, L denotes the length of the small release sheet (length in the longer side direction of the adhesive skin patch sheet), and CL1 denotes a line (cut line) that makes up the cut.

To use the adhesive skin patch sheet 1A, the first release sheet 41A is peeled first, whereupon the exposed pressure-sensitive adhesive layer 3A is applied. Peeling first the small first release sheet 41A, makes the exposed portion of the pressure-sensitive adhesive layer 3A smaller, so that the adhesive skin patch sheet 1A can be handled more easily as a result, thereby reducing the likelihood of wrinkling during applying of the exposed portion of the pressure-sensitive adhesive layer 3A.

The two ends of the cut line CL1 of the release sheet 4A are located, preferably, at positions distant by ⅓ to 1/20 from the respective ends (herein, ends on the side of the first release sheet 41A), in particular, at positions distant by ⅓ to 1/10 from the respective ends of the two opposing sides of the release sheet 4A, in the longer side direction.

By forming the cut line CL1 at such positions, the surface area of the pressure-sensitive adhesive layer 3A, which becomes exposed when the first release sheet 41A is peeled off, is small enough so as to prevent wrinkling of the adhesive skin patch sheet 1A that is applied in the first half of applying.

The cut line CL1 is shaped as a convexity only from the second release sheet 42A toward the first release sheet 41A. In the present embodiment, the cut line CL1 is convex overall, specifically in the shape of a circular arc.

When the cut line CL1 has the above shape, the inner ends of the second release sheet 42A (ends on the side of the first release sheet 41A) are also convex. To use the adhesive skin patch sheet 1A, the first release sheet 41A is peeled first, after which the exposed pressure-sensitive adhesive layer 3A is applied. Thereafter, the adhesive skin patch sheet 1A is bent, on the side of the support 2A, along the cut line CL1, to peel off the second release sheet 42A, as a result of which there juts out the convex portion of the inner end of the second release sheet 42A. This jutting portion is shown in FIG. 1(c) with horizontal hatching. The jutting portion can be easily picked with the fingers, which makes the second release sheet 42A easier to peel off.

Shaping the second release sheet 42A so as to be convex only toward the first release sheet 41A reduces the likelihood of nonuniform release force between the second release sheet 42A and the pressure-sensitive adhesive layer 3A during peeling of the second release sheet 42A from the pressure-sensitive adhesive layer 3A, thereby suppressing the formation of wrinkles in the adhesive skin patch sheet 1A.

The length D in the convex direction (longer side direction of the adhesive skin patch sheet 1A) of the convexity of the cut line CL1 in the release sheet 4A, namely the distance (D) in the convex direction between a point P on the cut line CL1, the point P is closest to the outer end (left end in FIG. 1(c)) of the first release sheet 41A, and points Q on the cut line CL1, the points Q are closest to the outer end (right end in FIG. 1(c)) of the second release sheet 42A, is preferably 5 to 25 mm, in particular 7 to 20 mm. The positions of both ends of the cut line CL1 (positions of a start point Q and an end point Q) are preferably symmetrical with respect to a symmetric axis that coincides with the centerline of the release sheet 4A in the longer side direction, but may also be asymmetrical. When the positions of both ends of the cut line CL1 are asymmetrical, the length D of the convexity of the cut line CL1 is the distance between the point P and the point Q that is farthest from the point P.

Setting the length D of the convexity of the cut line CL1 to lie within the above range makes it considerably easier to pick with the fingers the above-described jutting portion of the second release sheet 42A during the second half of applying. When the length D of the convexity of the cut line CL1 exceeds 25 mm, there increases the surface area of the portion of the pressure-sensitive adhesive layer 3A which is re-applied onto the adherend, during second-half applying, after having been peeled off following first-half applying of the pressure-sensitive adhesive layer 3A onto the adherend. This may lower the adhesive strength of the pressure-sensitive adhesive layer 3A. Specifically, to use the adhesive skin patch sheet 1A, the first release sheet 41A is peeled, whereupon the pressure-sensitive adhesive layer 3A exposed thereby is applied. Thereafter, the adhesive skin patch sheet 1A is bent, so that when the convex portion of the inner end of the second release sheet 42A juts out, the portion delimited by the line passing through the point P of the cut line CL1 in the width direction, the cut line CL1, and the edges of the first release sheet 41A in the longer side direction (portion hatched with vertical lines in FIG. 1(c)) must be temporarily peeled. When the length D of the convexity of the cut line CL1 exceeds 25 mm, however, the surface area of this portion is excessively large, which may impair the adhesive strength of the pressure-sensitive adhesive layer 3A.

To produce the adhesive skin patch sheet 1A, the material of the pressure-sensitive adhesive layer 3A is for instance applied onto the release-treated surface of the release sheet 4A using a coater such as a roller coater, a knife coater, a roll-knife coater, an air-knife coater, a die coater, a bar coater, a gravure coater, a curtain coater or the like, and then the support 2A is superposed onto the formed pressure-sensitive adhesive layer 3A, after which the cut line CL1 is cut only into the release sheet 4A, by half cutting, using a punching device or the like.

To use the adhesive skin patch sheet 1A, the first release sheet 41A is peeled first, whereupon the portion of the pressure-sensitive adhesive layer 3A exposed thereby is applied to the surface of the adherend (for instance, skin). The exposed portion of the pressure-sensitive adhesive layer 3A is small, and hence the adhesive skin patch sheet 1A can be handled more easily, thereby reducing the likelihood of wrinkling during applying of the exposed portion of the pressure-sensitive adhesive layer 3A.

Next, the adhesive skin patch sheet 1A is bent along the cut line CL1, on the side of the support 2A. As a result, the convex portion (horizontally hatched area in FIG. 1(c)) of the inner end of the second release sheet 42A juts out. This jutting portion is picked with the fingers, and the second release sheet 42A is gradually peeled from the inner end thereof toward the outer end, at the same time that the exposed pressure-sensitive adhesive surface is gradually applied onto the adherend surface.

Shaping the second release sheet 42A so as to be convex only toward the first release sheet 41A reduces the likelihood of wrinkle formation in the adhesive skin patch sheet 1A when the second release sheet 42A is peeled off and the pressure-sensitive adhesive layer 3A of the portion exposed thereby is applied onto the adherend surface.

Thus, the adhesive skin patch sheet 1A is excellent in handleability and little prone to form wrinkles during applying.

Second Embodiment

Figure 2:
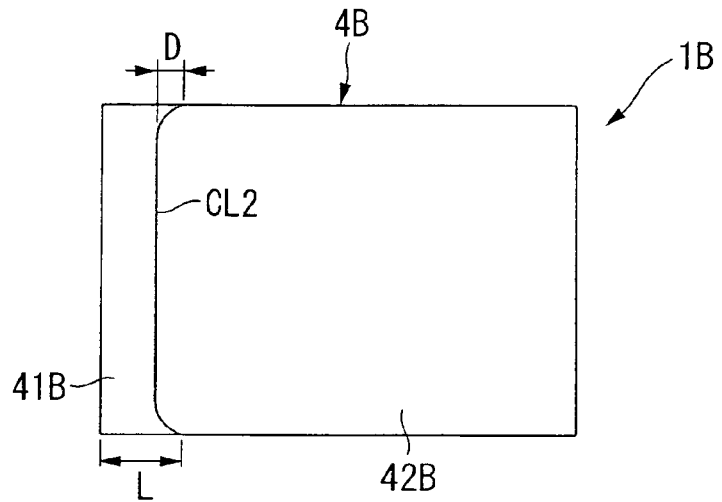
FIG. 2 is a bottom plan view of an adhesive skin patch sheet according to a second embodiment of the present invention.

FIG. 2 is a bottom plan view of an adhesive skin patch sheet according to a second embodiment of the present invention.

Except for the shape of a cut line CL2 formed in a release sheet 4B, an adhesive skin patch sheet 1B according to the present embodiment has the similar constitution as the adhesive skin patch sheet 1A according to the first embodiment above.

The cut line CL2 is shaped wholly as a convexity, only from a second release sheet 42B toward a first release sheet 41B. Specifically, the shape of the cut line CL2 is curved as a circular arc, on both ends of the cut line CL2, the two inner ends of the circular arcuate curves being joined by a straight line. The radius of curvature of arcuate curves ranges preferably from 2 to 25 mm.

The length of the convexity of the cut line CL2 in the convex direction (longer side direction of the adhesive skin patch sheet 1B), i.e. the linear distance from the straight-line portion of the cut line CL2 to both ends of the cut line CL2, is preferably similar to the length of the convexity of the cut line CL1, in the convex direction, in the first embodiment. The position of the cut line CL2 in the release sheet 4B is preferably similar to the position of the cut line CL1 in the release sheet 4A of the first embodiment.

Like the adhesive skin patch sheet 1A according to the first embodiment, the adhesive skin patch sheet 1B comprising a cut line CL2 such as the one described above is also excellent in handleability and little prone to form wrinkles during applying.

Third Embodiment

Figure 3:
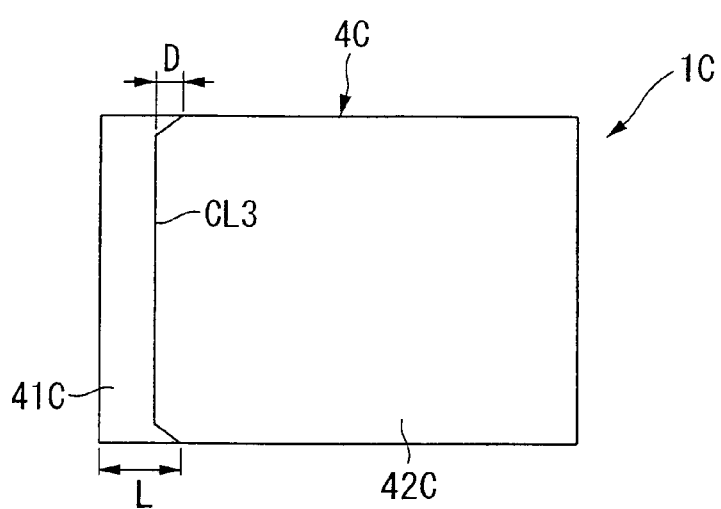
FIG. 3 is a bottom plan view of an adhesive skin patch sheet according to a third embodiment of the present invention.

FIG. 3 is a bottom plan view of an adhesive skin patch sheet according to a third embodiment of the present invention.

Except for the shape of a cut line CL3 formed in a release sheet 4C, an adhesive skin patch sheet 1C according to the present embodiment has the similar constitution as the adhesive skin patch sheet 1A according to the first embodiment above.

The cut line CL3 is shaped wholly as a convexity, only from a second release sheet 42C toward a first release sheet 41C. Specifically, the cut line CL3 is shaped as a bottom-less trapezoid whose two ends are formed obliquely to a gradually narrower width, the inner ends of these two oblique lines being joined by a straight line.

The length of the convexity of the cut line CL3 in the convex direction (longer side direction of the adhesive skin patch sheet 1C), i.e. the linear distance from the straight-line portion of the cut line CL3 to both ends of the cut line CL3, is preferably similar to the length of the convexity of the cut line CL1, in the convex direction, in the first embodiment. The position of the cut line CL3 in the release sheet 4C is preferably similar to the position of the cut line CL1 in the release sheet 4A of the first embodiment.

Like the adhesive skin patch sheet 1A according to the first embodiment, the adhesive skin patch sheet 1C comprising a cut line CL3 such as the one described above is also excellent in handleability and little prone to form wrinkles during applying.

Fourth Embodiment

Figure 4:
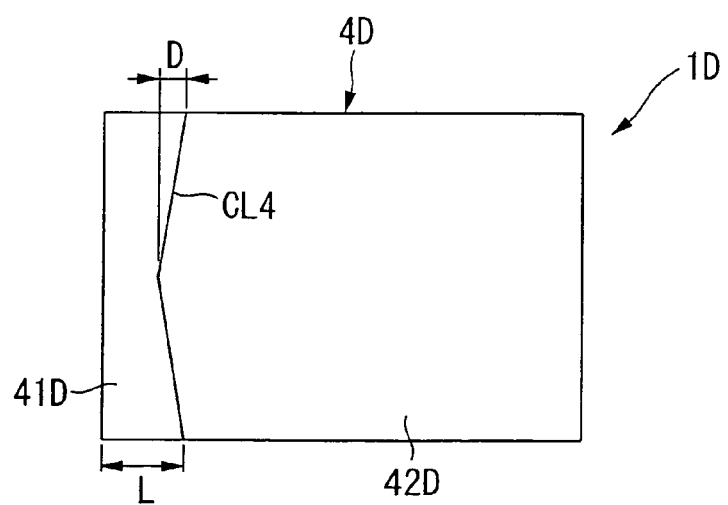
FIG. 4 is a bottom plan view of an adhesive skin patch sheet according to a fourth embodiment of the present invention.

FIG. 4 is a bottom plan view of an adhesive skin patch sheet according to a fourth embodiment of the present invention.

Except for the shape of a cut line CL4 formed in a release sheet 4D, an adhesive skin patch sheet 1D according to the present embodiment has the similar constitution as the adhesive skin patch sheet 1A according to the first embodiment above.

The cut line CL4 is also shaped wholly as a convexity, only from a second release sheet 42D toward a first release sheet 41D. Specifically, the cut line CL4 is shaped as a chevron with oblique lines slanting from both ends of the cut line CL4 toward the center thereof.

The length of the convexity of the cut line CL4 in the convex direction (longer side direction of the adhesive skin patch sheet 1D), i.e. the distance between the apex on the center of the cut line CL4 and a straight line that joins both ends of the cut line CL4, is preferably similar to the length of the convexity of the cut line CL1 in the convex direction in the first embodiment. The position of the cut line CL4 in the release sheet 4D is preferably similar to the position of the cut line CL1 in the release sheet 4A of the first embodiment.

Like the adhesive skin patch sheet 1A according to the first embodiment, the adhesive skin patch sheet 1D comprising a cut line CL4 such as the one described above is also excellent in handleability and little prone to form wrinkles during applying.

The apex of the cut line CL4 in the present embodiment is positioned at the center of the cut line CL4. The apex, however, is not limited thereto, and may be offset from the center of the cut line CL4. Specifically, the apex is located preferably at a position distant by 1/10 to 1/2 the length of release sheet 4A in the width direction, from either end of the cut line CL4.

Fifth Embodiment

FIGS. 5(a) and 5(b) are bottom plan views of an adhesive skin patch sheet according to a fifth embodiment of the present invention.

Except for the shape of a cut line CL5 formed in a release sheet 4E, an adhesive skin patch sheet 1E according to the present embodiment has the similar constitution as the adhesive skin patch sheet 1A according to the first embodiment above.

As shown in FIG. 5(a), the cut line CL5 according to the present embodiment is convexly shaped so as to be convex partially only from a second release sheet 42E to a first release sheet 41E. Specifically, the cut line CL5 comprises a substantially semicircular convexity 5E on the central portion of the cut line CL5, and a straight line portion other than the convexity 5E. In the present embodiment, the convexity 5E and the straight-line portion are smoothly joined by curved lines.

The length of the convexity 5E of the cut line CL5 in the convex direction (longer side direction of the adhesive skin patch sheet 1E), i.e. the distance between the apex of the convexity 5E of the cut line CL5 and both ends of the cut line CL5 in the convex direction, is preferably similar to the length of the convexity of the cut line CL1 in the convex direction in the first embodiment. The position of the cut line CL5 in the release sheet 4E is preferably similar to the position of the cut line CL1 in the release sheet 4A of the first embodiment.

The convexity 5E rises preferably from base points B at positions distant from respective ends of the cut line CL5 by 1/3 to ~1/50, in particular, from base points B at positions distant by 1/3 to 1/10, of the length of the release sheet 4E in the width direction. In other words, the values $W_2$ and $W_2'$ are preferably $W_1/3$ to $W_1/50$, in particular $W_1/3$ to $W_1/10$, wherein $W_1$ is the length of the cut line CL5 in the width direction of the release sheet 4E, and $W_2$ and $W_2'$ are the distances from the ends of the cut line CL5 up to the base points B, along the width direction of the release sheet 4E, the base-points B being the points at which the convexity 5E rises in the cut line CL5 (see FIG. 5(b)). $W_2$ and $W_2'$ are preferably of identical length, but may also be of dissimilar length.

By positioning thus the base points B, at which the convexity 5E rises, the convexity 5E has a predetermined width $(W_1-(W_2+W_2'))$ at a non-edge position, and thus the second release sheet 42E can be peeled with a smooth transition from peeling of the convexity 5E to peeling of the straight-line portion. As a result, this reduces the likelihood of nonuniform release force between the second release sheet 42E and the pressure-sensitive adhesive layer 3E, and suppresses thereby the formation of wrinkles in the adhesive skin patch sheet 1E.

Angles d formed between the tangents T of the line that makes up the convexity 5E and the straight-line portion, on the inward side of the convexity 5E, are defined as follows. In the case of the convexity 5E, the tangent $T_m$ for which the angle d is largest are the tangents T passing through inflection points R (see FIG. 5(b)). The angle $d_m$ formed between a tangent $T_m$ and the straight-line portion, on the inward side of the formed convexity 5E, ranges preferably from 5° to 90°, in particular from 15° to 90°.

As the result that the convexity 5E has a shape comprising a tangent $T_m$ which makes up the above-described angle $d_m$, the second release sheet 42E can be peeled with a smooth transition from peeling of the convexity 5E to peeling of the straight-line portion. This reduces, as a result, the likelihood of nonuniform release force between the second release sheet 42E and the pressure-sensitive adhesive layer 3E, and suppresses thereby the formation of wrinkles in the adhesive skin patch sheet 1E.

To use the adhesive skin patch sheet 1E, the first release sheet 41E is peeled first, whereupon the exposed portion of the pressure-sensitive adhesive layer 3E is applied to the surface of the adherend, after which the adhesive skin patch sheet 1E is bent along cut line CL5, on the side of the support 2E. As a result, the convexity 5E of the second release sheet 42E juts out. This jutting portion is picked with the fingers, and the second release sheet 42E is gradually peeled from the inner end thereof toward the outer end, at the same time that the exposed pressure-sensitive adhesive surface is gradually applied onto the adherend surface.

The likelihood of wrinkle formation in the adhesive skin patch sheet 1E, when the second release sheet 42E is peeled off and the pressure-sensitive adhesive layer 3E of the portion exposed thereby is applied onto the adherend surface, is reduced by shaping the second release sheet 42E so as to be convex only toward the first release sheet 41E, by prescribing a predetermined width for the convexity 5E at a non-edge position, and by shaping the convexity 5E so as to have a tangent $T_m$ that makes up the above-described angle $d_m$.

Thus, the adhesive skin patch sheet 1E is excellent in handleability and little prone to form wrinkles during applying.

Sixth Embodiment

FIG. 6 is a bottom plan view of an adhesive skin patch sheet according to a sixth embodiment of the present invention.

Except for the shape of a cut line CL6 formed on a release sheet 4F, an adhesive skin patch sheet 1F according to the present embodiment has the similar constitution as the adhesive skin patch sheet 1E according to the fifth embodiment above.

The cut line CL6 is convexly shaped so as to be convex partially only from a second release sheet 42F toward a first release sheet 41F. Specifically, the cut line CL6 comprises a convexity 5F shaped as a chevron (triangle without a base) in the central portion of the cut line CL6, and a straight-line portion elsewhere.

The angle d formed by the lines that make up convexity 5F and the straight-line portion, on the inward side of the convexity 5F, ranges preferably from 5° to 80°, in particular from 15° to 60°.

The second release sheet 42F can be peeled with a smooth transition from peeling of the convexity 5F to peeling of the straight-line portion, by shaping the convexity 5F so as to comprise lines that form the above-described angle d. This reduces, as a result, the likelihood of nonuniform release force between the second release sheet 42F and the pressure-sensitive adhesive layer 3F, and suppresses thereby the formation of wrinkles in the adhesive skin patch sheet 1F.

The position of the cut line CL6 in the release sheet 4F, the length of the convexity 5F of the cut line CL6 in the convex direction (longer side direction of the adhesive skin patch sheet 1F), i.e. the distance from the apex of the convexity 5F of the cut line CL6 to both ends of the cut line CL6, in the convex direction, as well as the positions of the base points B of the convexity 5F, are preferably similar to the position of the cut line CL5, the length of the convexity 5E in the convex direction, and the positions of the base points B, in the fifth embodiment.

Like the adhesive skin patch sheet 1E according to the fifth embodiment, the adhesive skin patch sheet 1F comprising a cut line CL6 such as the one described above is also excellent in handleability and little prone to form wrinkles during applying.

Seventh Embodiment

FIGS. 7(a) and 7(b) are bottom plan views of an adhesive skin patch sheet according to a seventh embodiment of the present invention.

Except for the shape of a cut line CL7 formed in a release sheet 4G, an adhesive skin patch sheet 1G according to the present embodiment has the similar constitution as the adhesive skin patch sheet 1E according to the fifth embodiment above.

In the present embodiment, the cut line CL7 is convexly shaped so as to be convex partially only from a second release sheet 42G toward a first release sheet 41G. Specifically, the cut line CL7 comprises a convexity 5G shaped as a rectangle (FIG. 7(a)) or as a trapezoid without a base (FIG. 7(b)), in the central portion of the cut line CL7, and a straight-line portion elsewhere.

The angle d formed by the oblique lines that make up convexity 5G and the straight-line portion, on the inward side of the convexity 5G, ranges preferably from 20° to 90°, in particular from 30° to 90°. The oblique lines (lines other than the upper base) are herein the lines that yield the largest angle d, among the lines that make up the convexity 5G.

The second release sheet 42G can be peeled with a smooth transition from peeling of the convexity 5G to peeling of the straight-line portion, by shaping the convexity 5G so as to comprise lines that form the above-described angle d. This reduces, as a result, the likelihood of nonuniform release force between the second release sheet 42G and the pressure-sensitive adhesive layer 3G, and suppresses thereby the formation of wrinkles in the adhesive skin patch sheet 1G.

The position of the cut line CL7 in the release sheet 4G, the length of the convexity 5G in the convex direction (longer side direction of the adhesive skin patch sheet 1G), i.e. the distance between the upper base of the convexity 5G of the cut line CL7 and both ends of the cut line CL7, in the convex direction, as well as the positions of the base points B of the convexity 5G, are preferably similar to the position of the cut line CL5, the length of the convexity 5E in the convex direction, and the positions of the base points B, in the fifth embodiment.

Like the adhesive skin patch sheet 1E according to the fifth embodiment, the adhesive skin patch sheet 1G comprising a cut line CL7 such as the one described above is also excellent in handleability and little prone to form wrinkles during applying.

Other Embodiments

The above embodiment has been described for facilitating understanding of the present invention, and not for limiting the present invention. The various elements described in the above embodiment are thus deemed to also include all design modifications and equivalents falling under the technical scope of the present invention.

For instance, the radius of curvature of the cut line CL1 in the first embodiment may be different for each position of the cut line CL1. Also, the corners of the cut line CL3 in the third embodiment, of the cut line CL4 in the fourth embodiment, of the cut line CL6 in the sixth embodiment, or of the cut line CL7 in the seventh embodiment, may be rounded.

EXAMPLES

Following is a more detailed description of the present invention through examples and so on; however, the scope of the present invention is not limited by those examples and so on.

Example 1

An ethyl acetate solution of a pressure-sensitive adhesive, having a styrene-isoprene-styrene copolymer as a main component, was applied onto a release sheet (bending resistance: 102 mm, JIS L1096-1999 cantilever method) obtained by subjecting a 75 μm-thick polyethylene terephthalate film to a silicone release treatment, and was dried to a thickness of 30 μm after drying, to form a pressure-sensitive adhesive layer. Thereafter, an expandable nonwoven fabric made of polyethylene terephthalate, having a basis weight of 100 g/m2, was superposed onto the obtained pressure-sensitive adhesive layer, to yield a sheet-like stock. The sheet-like stock was punched to yield a 70 mm×100 mm rectangle (with the four corners thereof rounded), whereupon a cut such as the cut line shape shown in FIG. 1A (both-end position of the cut line: ⅓=length L of the small release sheet: 33 mm, distance D: 20 mm) was cut into the release sheet alone, to yield an adhesive skin patch sheet.

Example 2

An adhesive skin patch sheet was obtained as in Example 1, except that herein the both-end position of the cut line of the release sheet of Example 1 was ¼ (=length L of the small release sheet: 25 mm), and the distance D was 12 mm.

Example 3

An adhesive skin patch sheet was obtained as in Example 1, except that herein the both-end position of the cut line of the release sheet of Example 1 was 1/10 (=length L of the small release sheet: 10 mm), and the distance D was 5 mm.

Example 4

An ethyl acetate solution of a pressure-sensitive adhesive, having a styrene-isoprene-styrene copolymer as a main component, was applied onto a release sheet (bending resistance: 102 mm, JIS L1096-1999 cantilever method) obtained by subjecting a 75 μm-thick polyethylene terephthalate film to a silicone release treatment, and was dried to a thickness of 30 μm after drying, to form a pressure-sensitive adhesive layer. Thereafter, an expandable nonwoven fabric made of polyethylene terephthalate, having a basis weight of 100 g/m$^2$, was superposed onto the obtained pressure-sensitive adhesive layer, to yield a sheet-like stock. The sheet-like stock was punched to yield a 70 mm×100 mm rectangle (with the four corners thereof rounded), whereupon a cut such as the cut line shape shown in FIG. 2 (both-end position of the cut line: ⅓=length L of the small release sheet: 33 mm, distance D: 20 mm, radius of curvature of circular arc portions: 5 mm) was cut into the release sheet alone, to yield an adhesive skin patch sheet.

Example 5

An adhesive skin patch sheet was obtained as in Example 4, except that herein the both-end position of the cut line of the release sheet of Example 4 was ¼ (=length L of the small release sheet: 25 mm), and the distance D was 12 mm.

Example 6

An adhesive skin patch sheet was obtained as in Example 4, except that herein the both-end position of the cut line of the release sheet of Example 4 was ⅒ (=length L of the small release sheet: 10 mm), and the distance D was 5 mm.

Example 7

An ethyl acetate solution of a pressure-sensitive adhesive, having a styrene-isoprene-styrene copolymer as a main component, was applied onto a release sheet (bending resistance: 102 mm, JIS L1096-1999 cantilever method) obtained by subjecting a 75 μm-thick polyethylene terephthalate film to a silicone release treatment, and was dried to a thickness of 30 μm after drying, to form a pressure-sensitive adhesive layer. Thereafter, an expandable nonwoven fabric made of polyethylene terephthalate, having a basis weight of 100 g/m², was superposed onto the obtained pressure-sensitive adhesive layer, to yield a sheet-like stock. The sheet-like stock was punched to yield a 70 mm×100 mm rectangle (with the four corners thereof rounded), whereupon a cut such as the cut line shape shown in FIG. 3 (both-end position of the cut line: ⅓=length L of the small release sheet: 33 mm, distance D: 20 mm) was cut into the release sheet alone, to yield an adhesive skin patch sheet.

Example 8

An adhesive skin patch sheet was obtained as in Example 7, except that herein the both-end position of the cut line of the release sheet of Example 7 was ¼ (=length L of the small release sheet: 25 mm), and the distance D was 12 mm.

Example 9

An adhesive skin patch sheet was obtained as in Example 7, except that herein the both-end position of the cut line of the release sheet of Example 7 was ⅒ (=length L of the small release sheet: 10 mm), and the distance D was 5 mm.

Example 10

An ethyl acetate solution of a pressure-sensitive adhesive, having a styrene-isoprene-styrene copolymer as a main component, was applied onto a release sheet (bending resistance: 102 mm, JIS L1096-1999 cantilever method) obtained by subjecting a 75 μm-thick polyethylene terephthalate film to a silicone release treatment, and was dried to a thickness of 30 μm after drying, to form a pressure-sensitive adhesive layer. Thereafter, an expandable nonwoven fabric made of polyethylene terephthalate, having a basis weight of 100 g/m², was superposed onto the obtained pressure-sensitive adhesive layer, to yield a sheet-like stock. The sheet-like stock was punched to yield a 70 mm×100 mm rectangle (with the four corners thereof rounded), whereupon a cut such as the cut line shape shown in FIG. 4 (both-end position of the cut line: ⅓=length L of the small release sheet: 33 mm, distance D: 20 mm) was cut into the release sheet alone, to yield an adhesive skin patch sheet.

Example 11

An adhesive skin patch sheet was obtained as in Example 10, except that herein the both-end position of the cut line of the release sheet of Example 10 was ¼ (=length L of the small release sheet: 25 mm), and the distance D was 12 mm.

Example 12

An adhesive skin patch sheet was obtained as in Example 10, except that herein the both-end position of the cut line of the release sheet of Example 10 was ⅒ (=length L of the small release sheet: 10 mm), and the distance D was 5 mm.

Example 13

An ethyl acetate solution of a pressure-sensitive adhesive, having a styrene-isoprene-styrene copolymer as a main component, was applied onto a release sheet (bending resistance: 102 mm, JIS L1096-1999 cantilever method) obtained by subjecting a 75 μm-thick polyethylene terephthalate film to a silicone release treatment, and was dried to a thickness of 30 μm after drying, to form a pressure-sensitive adhesive layer. Thereafter, an expandable nonwoven fabric made of polyethylene terephthalate, having a basis weight of 100 g/m², was superposed onto the obtained pressure-sensitive adhesive layer, to yield a sheet-like stock. The sheet-like stock was punched to yield a 70 mm×100 mm rectangle (with the four corners thereof rounded), whereupon a cut such as the cut line shape shown in FIG. 5 (both-end position of the cut line: ¼=length L of the small release sheet: 25 mm, distance D: 20 mm, positions of rising base points: ⅒=distances $W_2$, $W_2'$: 7 mm, angle d: 45°) was cut into the release sheet alone, to yield an adhesive skin patch sheet.

Example 14

An adhesive skin patch sheet was obtained as in Example 13, except that herein the both-end position of the cut line of the release sheet of Example 13 was ¼ (=length L of the small release sheet: 25 mm), the distance D was 12 mm, the positions of the rise base points were ¼ (=distances $W_2$, $W_2'$: 17.5 mm) and the angle d was 45°.

Example 15

An adhesive skin patch sheet was obtained as in Example 13, except that herein the both-end position of the cut line of the release sheet of Example 13 was ¼ (=length L of the small release sheet: 25 mm), the distance D was 5 mm, the positions of the rise base points were ⅖ (=distances $W_2$, $W_2'$: 28 mm) and the angle d was 45°.

Example 16

An ethyl acetate solution of a pressure-sensitive adhesive, having a styrene-isoprene-styrene copolymer as a main component, was applied onto a release sheet (bending resistance: 102 mm, JIS L1096-1999 cantilever method) obtained by subjecting a 75 μm-thick polyethylene terephthalate film to a silicone release treatment, and was dried to a thickness of 30 μm after drying, to form a pressure-sensitive adhesive layer. Thereafter, an expandable nonwoven fabric made of polyethylene terephthalate, having a basis weight of 100 g/m², was superposed onto the obtained pressure-sensitive adhesive layer, to yield a sheet-like stock. The sheet-like stock was punched to yield a 70 mm×100 mm rectangle (with the four corners thereof rounded), whereupon a cut such as the cut line shape shown in FIG. 6 (both-end position of the cut line: ¼=length L of the small release sheet: 25 mm, distance D: 12 mm, positions of rising base points: ⅕=distances $W_2$, $W_2$': 14 mm, angle d: 30°) was cut into the release sheet alone, to yield an adhesive skin patch sheet.

Example 17

An adhesive skin patch sheet was obtained as in Example 16, except that herein the both-end position of the cut line of the release sheet of Example 16 was ¼ (=length L of the small release sheet: 25 mm), the distance D was 12 mm, the positions of the rise base points were ⅓ (=distances $W_2$, $W_2$': 23 mm) and the angle d was 45°.

Example 18

An adhesive skin patch sheet was obtained as in Example 16, except that herein the both-end position of the cut line of the release sheet of Example 16 was ¼ (=length L of the small release sheet: 25 mm), the distance D was 12 mm, the positions of the rise base points were ⅖ (=distances $W_2$, $W_2$': 28 mm) and the angle d was 60°.

Example 19

An ethyl acetate solution of a pressure-sensitive adhesive, having a styrene-isoprene-styrene copolymer as a main component, was applied onto a release sheet (bending resistance: 102 mm, JIS L1096-1999 cantilever method) obtained by subjecting a 75 μm-thick polyethylene terephthalate film to a silicone release treatment, and was dried to a thickness of 30 μm after drying, to form a pressure-sensitive adhesive layer. Thereafter, an expandable nonwoven fabric made of polyethylene terephthalate, having a basis weight of 100 g/m², was superposed onto the obtained pressure-sensitive adhesive layer, to yield a sheet-like stock. The sheet-like stock was punched to yield a 70 mm×100 mm rectangle (with the four corners thereof rounded), whereupon a cut such as the cut line shape shown in FIG. 7 (both-end position of the cut line: ¼=length L of the small release sheet: 25 mm, distance D: 12 mm, positions of rising base points: ¹⁄₃₅=distances $W_2$, $W_2$': 2 mm, angle d: 90°) was cut into the release sheet alone, to yield an adhesive skin patch sheet.

Example 20

An adhesive skin patch sheet was obtained as in Example 19, except that herein the both-end position of the cut line of the release sheet of Example 19 was ¼ (=length L of the small release sheet: 25 mm), the distance D was 12 mm, the positions of the rise base points were ¹⁄₁₀ (=distances $W_2$, $W_2$': 7 mm) and the angle d was 90°.

Example 21

An adhesive skin patch sheet was obtained as in Example 19, except that herein the both-end position of the cut line of the release sheet of Example 19 was ¼ (=length L of the small release sheet: 25 mm), the distance D was 12 mm, the positions of the rise base points were ⅓ (=distances $W_2$, $W_2$': 23 mm) and the angle d was 90°.

Example 22

An ethyl acetate solution of a pressure-sensitive adhesive, having a styrene-isoprene-styrene copolymer as a main component, was applied onto a release sheet (bending resistance: 102 mm, JIS L1096-1999 cantilever method) obtained by subjecting a 75 μm-thick polyethylene terephthalate film to a silicone release treatment, and was dried to a thickness of 30 μm after drying, to form a pressure-sensitive adhesive layer. Thereafter, an expandable nonwoven fabric made of polyethylene terephthalate, having a basis weight of 100 g/m², was superposed onto the obtained pressure-sensitive adhesive layer, to yield a sheet-like stock. The sheet-like stock was punched to yield a 70 mm×100 mm rectangle (with the four corners thereof rounded), whereupon a cut such as the cut line shape shown in FIG. 7 (both-end position of the cut line: ¼=length L of the small release sheet: 25 mm, distance D: 12 mm, positions of rising base points: ¹⁄₁₀=distances $W_2$, $W_2$': 7 mm, angle d: 30°) was cut into the release sheet alone, to yield an adhesive skin patch sheet.

Example 23

An adhesive skin patch sheet was obtained as in Example 22, except that herein the both-end position of the cut line of the release sheet of Example 22 was ¼ (=length L of the small release sheet: 25 mm), the distance D was 12 mm, the positions of the rise base points were ⅓ (=distances $W_2$, $W_2$': 23 mm) and the angle d was 45°.

Example 24

An adhesive skin patch sheet was obtained as in Example 22, except that herein the both-end position of the cut line of the release sheet of Example 22 was ¼ (=length L of the small release sheet: 25 mm), the distance D was 12 mm, the positions of the rise base points were ⅓ (=distances $W_2$, $W_2$': 23 mm) and the angle d was 60°.

Comparative Example 1

Figure 8:
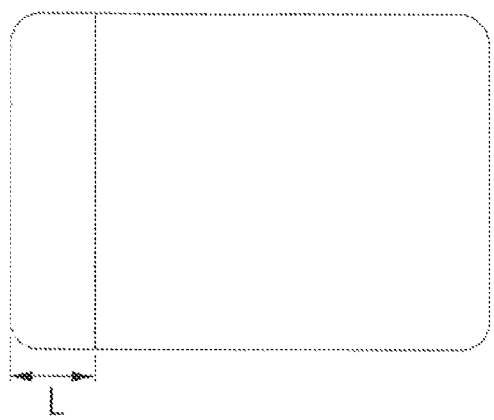
FIG. 8 is a bottom plan view of an adhesive skin patch sheet according to Comparative examples 1 to 3.

An ethyl acetate solution of a pressure-sensitive adhesive, having a styrene-isoprene-styrene copolymer as a main component, was applied onto a release sheet (bending resistance: 102 mm, JIS L1096-1999 cantilever method) obtained by subjecting a 75 μm-thick polyethylene terephthalate film to a silicone release treatment, and was dried to a thickness of 30 μm after drying, to form a pressure-sensitive adhesive layer. Thereafter, an expandable nonwoven fabric made of polyethylene terephthalate, having a basis weight of 100 g/m², was superposed onto the obtained pressure-sensitive adhesive layer, to yield a sheet-like stock. The sheet-like stock was punched to yield a 70 mm×100 mm rectangle (with the four corners thereof rounded), whereupon a cut such as the cut line shape (straight line) shown in FIG. 8 (both-end position of the cut line: ⅓=length L of the small release sheet: 33 mm) was cut into the release sheet alone, to yield an adhesive skin patch sheet.

Comparative Example 2

An adhesive skin patch sheet was obtained as in Comparative example 1, except that herein the both-end position of the cut line of the release sheet of Comparative example 1 was ¼ (=length L of the small release sheet: 25 mm).

Comparative Example 3

An adhesive skin patch sheet was obtained as in Comparative example 1, except that herein the both-end position of the cut line of the release sheet of Comparative example 1 was ¹⁄₁₀ (=length L of the small release sheet: 10 mm).

Comparative Example 4

Figure 9:
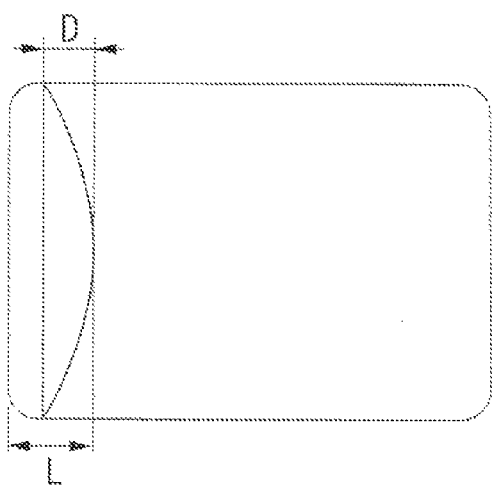
FIG. 9 is a bottom plan view of an adhesive skin patch sheet according to Comparative examples 4 to 7.

An ethyl acetate solution of a pressure-sensitive adhesive, having a styrene-isoprene-styrene copolymer as a main component, was applied onto a release sheet (bending resistance: 102 mm, JIS L1096-1999 cantilever method) obtained by subjecting a 75 μm-thick polyethylene terephthalate film to a silicone release treatment, and was dried to a thickness of 30 μm after drying, to form a pressure-sensitive adhesive layer. Thereafter, an expandable nonwoven fabric made of polyethylene terephthalate, having a basis weight of 100 g/m², was superposed onto the obtained pressure-sensitive adhesive layer, to yield a sheet-like stock. The sheet-like stock was punched to yield a 70 mm×100 mm rectangle (with the four corners thereof rounded), whereupon a cut such as the cut line shape (concave circular arc across whole sheet) shown in FIG. 9 (both-end position of the cut line: ½=length L of the small release sheet: 50 mm, distance D: 20 mm) was cut into the release sheet alone, to yield an adhesive skin patch sheet.

Comparative Example 5

An adhesive skin patch sheet was obtained as in Comparative example 4, except that herein the both-end position of the cut line of the release sheet of Comparative example 4 was ⅓ (=length L of the small release sheet: 33 mm), and the distance D was 20 mm.

Comparative Example 6

An adhesive skin patch sheet was obtained as in Comparative example 4, except that herein the both-end position of the cut line of the release sheet of Comparative example 4 was ¼ (=length L of the small release sheet: 25 mm), and the distance D was 12 mm.

Comparative Example 7

An adhesive skin patch sheet was obtained as in Comparative example 4, except that herein the both-end position of the cut line of the release sheet of Comparative example 4 was 1/10 (=length L of the small release sheet: 10 mm), and the distance D was 5 mm.

Comparative Example 8

Figure 10:
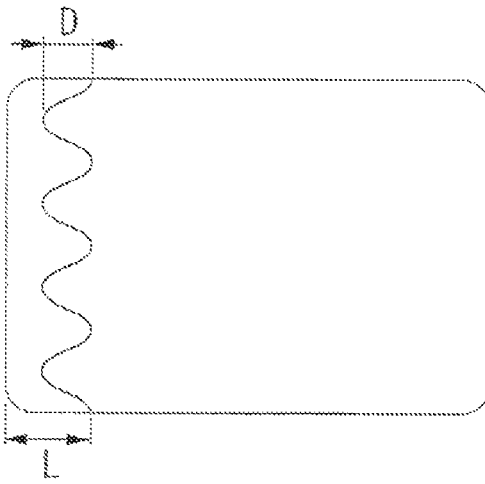
FIG. 10 is a bottom plan view of an adhesive skin patch sheet according to Comparative examples 8 to 10.

An ethyl acetate solution of a pressure-sensitive adhesive, having a styrene-isoprene-styrene copolymer as a main component, was applied onto a release sheet (bending resistance: 102 mm, JIS L1096-1999 cantilever method) obtained by subjecting a 75 μm-thick polyethylene terephthalate film to a silicone release treatment, and was dried to a thickness of 30 μm after drying, to form a pressure-sensitive adhesive layer. Thereafter, an expandable nonwoven fabric made of polyethylene terephthalate, having a basis weight of 100 g/m², was superposed onto the obtained pressure-sensitive adhesive layer, to yield a sheet-like stock. The sheet-like stock was punched to yield a 70 mm×100 mm rectangle (with the four corners thereof rounded), whereupon a cut such as the cut line shape (wavy shape) shown in FIG. 10 (both-end position of the cut line: ⅓=length L of the small release sheet: 33 mm, distance D: 10 mm) was cut into the release sheet alone, to yield an adhesive skin patch sheet.

Comparative Example 9

An adhesive skin patch sheet was obtained as in Comparative example 8, except that herein the both-end position of the cut line of the release sheet of Comparative example 8 was ¼ (=length L of the small release sheet: 25 mm).

Comparative Example 10

An adhesive skin patch sheet was obtained as in Comparative example 8, except that herein the both-end position of the cut line of the release sheet of Comparative example 8 was 1/10 (=length L of the small release sheet: 10 mm).

The above examples and comparative examples are summarized in Table 1.

TABLE 1

| | Shape | L (mm) | D (mm) | d (°) | $W_2, W_2'$ (mm) |
|---|---|---|---|---|---|
| Example 1 | | 33 | 20 | | |
| Example 2 | | 25 | 12 | | |
| Example 3 | | 10 | 5 | | |
| Example 4 | | 33 | 20 | | |
| Example 5 | | 25 | 12 | | |
| Example 6 | | 10 | 5 | | |
| Example 7 | | 33 | 20 | | |
| Example 8 | | 25 | 12 | | |
| Example 9 | | 10 | 5 | | |
| Example 10 | | 33 | 20 | | |
| Example 11 | | 25 | 12 | | |
| Example 12 | | 10 | 5 | | |

TABLE 1-continued

| | Shape | L (mm) | D (mm) | d (°) | $W_2, W_2'$ (mm) |
|---|---|---|---|---|---|
| Example 13 | 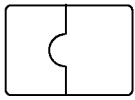 | 25 | 20 | 45 | 7 |
| Example 14 | | 25 | 12 | 45 | 17.5 |
| Example 15 | | 25 | 5 | 45 | 28 |
| Example 16 | 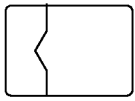 | 25 | 12 | 30 | 14 |
| Example 17 | | 25 | 12 | 45 | 23 |
| Example 18 | | 25 | 12 | 60 | 28 |
| Example 19 | 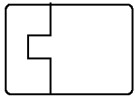 | 25 | 12 | 90 | 2 |
| Example 20 | | 25 | 12 | 90 | 7 |
| Example 21 | | 25 | 12 | 90 | 23 |
| Example 22 | 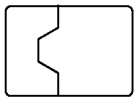 | 25 | 12 | 30 | 7 |
| Example 23 | | 25 | 12 | 45 | 23 |
| Example 24 | | 25 | 12 | 60 | 23 |
| Comp. ex. 1 |  | 33 | 0 | | |
| Comp. ex. 2 | | 25 | 0 | | |
| Comp. ex. 3 | | 10 | 0 | | |
| Comp. ex. 4 |  | 50 | 20 | | |
| Comp. ex. 5 | | 33 | 20 | | |
| Comp. ex. 6 | | 25 | 12 | | |
| Comp. ex. 7 | | 10 | 5 | | |
| Comp. ex. 8 |  | 33 | | | |
| Comp. ex. 9 | | 25 | | | |
| Comp. ex. 10 | | 10 | | | |

Test Example 1

The small release sheets of the adhesive skin patch sheets obtained in the examples or comparative examples were peeled, and then the pressure-sensitive adhesive layers of the exposed portions were applied onto people's elbow skin, as the adherend. Next, the adhesive skin patch sheets 1 were bent along the cut lines, on the side of the nonwoven fabric, and the large release sheets were peeled gradually from the inner end thereof toward the outer end, at the same time that the exposed pressure-sensitive adhesive surface was gradually applied onto the adherend surface.

The three items below were then evaluated.

1. Ease of Applying

The ease of applying of the adhesive skin patch sheet onto the skin was evaluated.

5 points . . . very easy applying.
4 points . . . fairly easy applying.
3 points . . . easy applying.
2 points . . . somewhat difficult applying.
1 point . . . very difficult applying.

2. Adhesion Between Pressure-Sensitive Adhesive Surfaces

Adhesion between pressure-sensitive adhesive surfaces during applying of the adhesive skin patch sheets onto the skin was evaluated.

5 points . . . no adhesion observed between pressure-sensitive adhesive surfaces.

4 points . . . slight adhesion observed between pressure-sensitive adhesive surfaces, but without practical influence.

3 points . . . adhesion observed between pressure-sensitive adhesive surfaces, with some practical influence.

2 points . . . adhesion observed between pressure-sensitive adhesive surfaces, with substantial practical influence.

1 point . . . adhesion observed between pressure-sensitive adhesive surfaces, to a level precluding practical use.

3. Wrinkling

Wrinkling of the adhesive skin patch sheet upon applying on the skin was evaluated.

5 points . . . no wrinkles.
4 points . . . fine wrinkles, but not uncomfortable during use.
3 points . . . fine wrinkles, uncomfortable during use.
2 points . . . large wrinkles, uncomfortable during use.
1 point . . . large wrinkles, to a level precluding practical use.

The evaluation results are shown in Table 2. The evaluation results are the average results of two applying tests. The adhesive skin patch sheets were judged to be suitable for use as adhesive skin patch sheets having excellent handleability, when the total score for the three items was 12 or higher.

TABLE 2

|  | Ease of applying | Adhesion between adhesive surfaces | Wrinkling | Total score |
|---|---|---|---|---|
| Example 1 | 5 | 5 | 5 | 15 |
| Example 2 | 5 | 5 | 5 | 15 |
| Example 3 | 4 | 5 | 5 | 14 |
| Example 4 | 5 | 4 | 5 | 14 |
| Example 5 | 5 | 4 | 5 | 14 |
| Example 6 | 4 | 4 | 5 | 13 |
| Example 7 | 5 | 4 | 5 | 14 |
| Example 8 | 5 | 4 | 5 | 14 |
| Example 9 | 4 | 4 | 5 | 13 |
| Example 10 | 5 | 5 | 5 | 15 |
| Example 11 | 5 | 5 | 5 | 15 |
| Example 12 | 4 | 5 | 5 | 14 |
| Example 13 | 5 | 5 | 5 | 15 |
| Example 14 | 5 | 5 | 5 | 15 |
| Example 15 | 5 | 4 | 4 | 13 |
| Example 16 | 4 | 4 | 4 | 12 |
| Example 17 | 4 | 4 | 4 | 12 |
| Example 18 | 4 | 4 | 4 | 12 |
| Example 19 | 4 | 4 | 4 | 12 |
| Example 20 | 4 | 4 | 4 | 12 |
| Example 21 | 4 | 4 | 4 | 12 |
| Example 22 | 5 | 4 | 5 | 14 |
| Example 23 | 5 | 4 | 5 | 14 |
| Example 24 | 5 | 4 | 5 | 14 |
| Comp. ex. 1 | 2 | 3 | 3 | 8 |
| Comp. ex. 2 | 2 | 3 | 3 | 8 |
| Comp. ex. 3 | 2 | 3 | 2 | 7 |
| Comp. ex. 4 | 2 | 3 | 2 | 7 |
| Comp. ex. 5 | 2 | 3 | 2 | 7 |
| Comp. ex. 6 | 2 | 3 | 2 | 7 |
| Comp. ex. 7 | 3 | 3 | 3 | 9 |
| Comp. ex. 8 | 3 | 3 | 3 | 9 |
| Comp. ex. 9 | 3 | 3 | 2 | 8 |
| Comp. ex. 10 | 3 | 3 | 2 | 8 |

As shown in Table 2, the adhesive skin patch sheets obtained in the examples were suitable for use as adhesive skin patch sheets having excellent handleability.

The adhesive skin patch sheet of the present invention can be used, for instance, in adhesive patches applied to the skin surface, preferably, for instance, in anti-inflammatory analgesic adhesive patches.

What is claimed is:

1. An adhesive skin patch sheet comprising a flexible support, a pressure-sensitive adhesive layer and a release sheet,
    wherein only one cut is provided on either an X-axis direction or a Y-axis direction of the release sheet,
    the release sheet is divided by the cut into two release sheets including a large release sheet and a small release sheet,
    a line making up the cut being formed so as to be convex only from the large release sheet toward the small release sheet,
    the large release sheet and the small release sheet cover the pressure-sensitive adhesive layer without overlapping each other, and
    the large release sheet has a most convex point formed by the line, and the large release sheet contacts the pressure-sensitive adhesive layer at least at the most convex point thereof.

2. The adhesive skin patch sheet according to claim 1, wherein the length of a convexity of the line making up the cut in a convex direction is 5 to 25 mm.

3. The adhesive skin patch sheet according to claim 1, wherein the shape of the line making up the cut has a convexity that is partially convex from the large release sheet toward the small release sheet.

4. The adhesive skin patch sheet according to claim 3, wherein the convexity rises from base points respectively located at positions distant by ⅓ to ¹⁄₅₀ of the length of the release sheet in the direction of the line making up the cut, from the ends of the line.

5. The adhesive skin patch sheet according to claim 3, wherein the line making up the cut comprises the convexity and a straight-line portion other than the convexity, and
    an angle formed between the straight-line portion and the line making up the convexity or a tangent of the line making up the convexity, on the inward side of the convexity, being the largest angle, ranges from 5° to 90°.

6. An adhesive skin patch sheet comprising a flexible support, a pressure-sensitive adhesive layer and a release sheet, wherein:
    only one cut is provided on either an X-axis direction or a Y-axis direction of the release sheet,
    the release sheet is divided by the cut into two release sheets including a large release sheet and a small release sheet,
    a line making up the cut being formed so as to be convex only from the large release sheet toward the small release sheet,
    the large release sheet and the small release sheet cover the pressure-sensitive adhesive layer without overlapping each other,
    the large release sheet has a most convex point formed by the line, and the large release sheet contacts the pressure-sensitive adhesive layer at least at the most convex point thereof,
    the pressure-sensitive adhesive layer and the release sheet are substantially shaped, in a plan view, as rectangles of substantially identical size, and
    both ends of the line making up the cut are respectively located at positions distant from ends of two opposing sides of the release sheet by ⅓ to ¹⁄₂₀ of the length thereof.

7. An adhesive skin patch sheet comprising a flexible support, a pressure-sensitive adhesive layer and a release sheet, wherein:
    only one cut is provided on either an X-axis direction or a Y-axis direction of the release sheet,
    the release sheet is divided by the cut into two release sheets including a large release sheet and a small release sheet,
    a line making up the cut being formed so as to be convex only from the large release sheet toward the small release sheet,
    the large release sheet and the small release sheet cover the pressure-sensitive adhesive layer without overlapping each other,
    the large release sheet has a most convex point formed by the line, and the large release sheet contacts the pressure-sensitive adhesive layer at least at the most convex point thereof, and
    the line making up the cut is wholly convex from the large release sheet toward the small release sheet.

* * * * *